(12) United States Patent
Hakimimehr et al.

(10) Patent No.: US 10,159,768 B2
(45) Date of Patent: Dec. 25, 2018

(54) MULTI-LAYER BIODEGRADABLE DEVICE HAVING ADJUSTABLE DRUG RELEASE PROFILE

(71) Applicant: BioInspire Technologies, Inc., Palo Alto, CA (US)

(72) Inventors: Dorna Hakimimehr, San Francisco, CA (US); Kyle Hammerick, San Jose, CA (US)

(73) Assignee: BioInspire Technologies, Inc., Palo Alto, CA (US)

( * ) Notice: Subject to any disclaimer, the term of this patent is extended or adjusted under 35 U.S.C. 154(b) by 13 days.

(21) Appl. No.: 15/624,304

(22) Filed: Jun. 15, 2017

(65) Prior Publication Data

US 2017/0281833 A1    Oct. 5, 2017

Related U.S. Application Data

(60) Continuation of application No. 15/046,285, filed on Feb. 17, 2016, now Pat. No. 9,682,174, which is a
(Continued)

(51) Int. Cl.
*A61F 13/15*     (2006.01)
*A61K 9/70*      (2006.01)
(Continued)

(52) U.S. Cl.
CPC ............ *A61L 31/046* (2013.01); *A61B 17/24* (2013.01); *A61K 9/0002* (2013.01);
(Continued)

(58) Field of Classification Search
None
See application file for complete search history.

(56) References Cited

U.S. PATENT DOCUMENTS 4,298,598 A    11/1981   Schwarz et al.
4,362,567 A    12/1982   Schwarz et al.
(Continued)

FOREIGN PATENT DOCUMENTS

EP    1 171 177 B1    1/2002
EP    1 759 723 B1    3/2007
(Continued)

OTHER PUBLICATIONS

Atrah, H. I., "Fibrin Glue," BMJ, (1994), 308:933.
(Continued)

*Primary Examiner* — Jeffrey T. Palenik
(74) *Attorney, Agent, or Firm* — Foley & Lardner LLP; Christopher C. Bolten; Nicola A. Pisano

(57) ABSTRACT

Methods and apparatus for a biodegradable multi-layer device suitable for medical applications are provided, wherein the device is formed from multiple film-layers configured to have different characteristics from one another such as different release profiles for therapeutic agents, adhesive properties, stiffness properties, and solubility properties. The film-layers may include a solid fibrinogen component. A device having multiple film-layers may take a non-adherent form during delivery to a target location within or on tissue, and thereafter may be exposed to moisture to take an adherent form on the tissue. The device may include a number of additives, including materials to improve the mechanical properties of the device, or one or more therapeutic or contrast agents.

19 Claims, 8 Drawing Sheets

Related U.S. Application Data division of application No. 13/794,355, filed on Mar. 11, 2013, now Pat. No. 9,271,925.

(51) Int. Cl.

| | | |
|---|---|---|
| *A61L 15/16* | (2006.01) | |
| *A61K 38/36* | (2006.01) | |
| *A61K 35/14* | (2015.01) | |
| *A61B 17/24* | (2006.01) | |
| *A61L 31/04* | (2006.01) | |
| *A61K 9/00* | (2006.01) | |
| *A61L 31/14* | (2006.01) | |
| *A61L 31/16* | (2006.01) | |
| *A61K 31/56* | (2006.01) | |
| *A61L 31/02* | (2006.01) | |
| *A61L 31/06* | (2006.01) | |
| *A61L 31/08* | (2006.01) | |
| *A61M 31/00* | (2006.01) | |

(52) U.S. Cl.
CPC ........... *A61K 9/0043* (2013.01); *A61K 31/56* (2013.01); *A61L 31/028* (2013.01); *A61L 31/047* (2013.01); *A61L 31/06* (2013.01); *A61L 31/08* (2013.01); *A61L 31/148* (2013.01); *A61L 31/16* (2013.01); *A61M 31/002* (2013.01); *A61L 2300/41* (2013.01); *A61L 2300/416* (2013.01); *A61L 2300/606* (2013.01); *A61L 2300/608* (2013.01); *A61L 2300/61* (2013.01); *A61L 2420/08* (2013.01); *Y10T 156/10* (2015.01)

(56) References Cited

U.S. PATENT DOCUMENTS

| | | |
|---|---|---|
| 4,377,572 A | 3/1983 | Schwarz et al. |
| 4,453,939 A | 6/1984 | Zimmerman et al. |
| 4,548,736 A | 10/1985 | Muller et al. |
| 4,560,374 A | 12/1985 | Hammerslag |
| 4,577,631 A | 3/1986 | Kreamer |
| 5,092,841 A | 3/1992 | Spears |
| 5,100,429 A | 3/1992 | Sinofsky et al. |
| 5,213,580 A | 5/1993 | Slepian et al. |
| 5,223,420 A | 6/1993 | Rabaud et al. |
| 5,487,897 A | 1/1996 | Polson et al. |
| 5,510,077 A | 4/1996 | Dinh et al. |
| 5,575,815 A | 11/1996 | Slepian et al. |
| 5,591,224 A | 1/1997 | Schwartz et al. |
| 5,591,227 A | 1/1997 | Dinh et al. |
| 5,599,307 A | 2/1997 | Bacher et al. |
| 5,634,936 A | 6/1997 | Linden et al. |
| 5,634,946 A | 6/1997 | Slepian |
| 5,651,982 A | 7/1997 | Marx |
| 5,693,085 A | 12/1997 | Buirge et al. |
| 5,733,563 A | 3/1998 | Fortier |
| 5,762,625 A | 6/1998 | Igaki |
| 5,792,106 A | 8/1998 | Mische |
| 5,899,917 A | 5/1999 | Edwards et al. |
| 5,942,278 A | 8/1999 | Hagedorn et al. |
| 6,039,757 A | 3/2000 | Edwards et al. |
| 6,054,122 A | 4/2000 | MacPhee et al. |
| 6,177,126 B1 | 1/2001 | Hagedorn et al. |
| 6,290,729 B1 | 9/2001 | Slepian et al. |
| 6,312,457 B1 | 11/2001 | DiMatteo et al. |
| 6,514,283 B2 | 2/2003 | DiMatteo et al. |
| 6,893,431 B2 | 5/2005 | Naimark et al. |
| 6,965,014 B1 | 11/2005 | Delmotte et al. |
| 7,044,982 B2 | 5/2006 | Milbocker |
| 7,057,019 B2 | 6/2006 | Pathak |
| 7,060,087 B2 | 6/2006 | DiMatteo et al. |
| 7,098,315 B2 | 8/2006 | Schaufler |
| 7,399,483 B2 | 7/2008 | Stimmeder |
| 7,402,172 B2 | 7/2008 | Chin et al. |
| 7,442,397 B2 | 10/2008 | Zhang |
| 7,481,788 B2 | 1/2009 | Naimark et al. |
| 7,544,192 B2 | 6/2009 | Eaton et al. |
| 7,572,769 B2 | 8/2009 | Rapp et al. |
| 7,597,882 B2 | 10/2009 | Pathak et al. |
| 7,662,141 B2 | 2/2010 | Eaton et al. |
| 7,662,142 B2 | 2/2010 | Eaton et al. |
| 7,662,409 B2 | 2/2010 | Masters |
| 7,682,382 B2 | 3/2010 | DiMatteo et al. |
| 7,686,798 B2 | 3/2010 | Eaton et al. |
| 7,691,094 B2 | 4/2010 | Eaton et al. |
| 7,727,547 B2 | 6/2010 | Fortune et al. |
| 7,771,409 B2 | 8/2010 | Chang et al. |
| 7,780,980 B2 | 8/2010 | Sawhney |
| 7,951,132 B2 | 5/2011 | Eaton et al. |
| 7,951,194 B2 | 5/2011 | Gueriguian et al. |
| 8,529,941 B2 | 9/2013 | Hakimimehr et al. |
| 8,563,510 B2 | 10/2013 | Hakimimehr et al. |
| 8,663,192 B2 | 3/2014 | Hester et al. |
| 8,740,929 B2 | 6/2014 | Gopferich et al. |
| 8,763,222 B2 | 7/2014 | Abbate et al. |
| 8,764,709 B2 | 7/2014 | Chang et al. |
| 8,795,713 B2 | 8/2014 | Makower et al. |
| 9,072,681 B2 | 7/2015 | Hakimimehr et al. |
| 9,084,876 B2 | 7/2015 | Makower et al. |
| 9,192,698 B2 | 11/2015 | Hakimimehr et al. |
| 9,241,834 B2 | 1/2016 | Chang et al. |
| 9,271,925 B2 | 3/2016 | Hakimimehr et al. |
| 9,370,649 B2 | 6/2016 | Chang et al. |
| 9,381,270 B2 | 7/2016 | Makower et al. |
| 9,446,103 B2 | 9/2016 | Hakimimehr et al. |
| 9,682,174 B2 * | 6/2017 | Hakimimehr ........ A61K 9/0002 |
| 9,713,658 B2 * | 7/2017 | Hakimimehr ........ A61K 9/7007 |
| 2003/0158607 A1 | 8/2003 | Carr et al. |
| 2005/0032205 A1 | 2/2005 | Smith et al. |
| 2005/0277577 A1 | 12/2005 | Hunter et al. |
| 2008/0200948 A1 | 8/2008 | Utecht et al. |
| 2009/0098176 A1 | 4/2009 | Helmus et al. |
| 2009/0216264 A1 | 8/2009 | Friedman et al. |
| 2009/0311338 A1 | 12/2009 | Pathak et al. |
| 2011/0071498 A1 | 3/2011 | Hakimimehr et al. |
| 2011/0071499 A1 | 3/2011 | Hakimimehr et al. |
| 2012/0101429 A1 | 4/2012 | Eaton et al. |
| 2012/0148658 A1 | 6/2012 | MacPhee et al. |
| 2012/0209319 A1 | 8/2012 | Bianco-Peled et al. |
| 2014/0154236 A1 | 6/2014 | Hester et al. |

FOREIGN PATENT DOCUMENTS

| | | |
|---|---|---|
| WO | WO-92/13495 A1 | 8/1992 |
| WO | WO-96/22115 A1 | 7/1996 |
| WO | WO-97/15188 A1 | 5/1997 |
| WO | WO-97/28832 A1 | 8/1997 |
| WO | WO-97/37694 A1 | 10/1997 |
| WO | WO-99/59647 A1 | 11/1999 |
| WO | WO-02/058750 A2 | 8/2002 |
| WO | WO-2007/029913 A1 | 3/2007 |
| WO | WO-2008/019126 | 2/2008 |
| WO | WO-2012/149492 A1 | 11/2012 |

OTHER PUBLICATIONS

Cederholm-Williams, S.A., "Fibrin Glue", BMJ, (1994), 308:1570.

PCT International Search Report and Written Opinion dated Jun. 18, 2014 in related PCT Patent Appl No. PCT/US2014/020021.

Thompson et al., "Fibrin Glue: A Review of its Preparation, Efficacy, and Adverse Effects as a Topical Hemostat," Drug Intell Clin. Pharm., (1988), 22:946-952.

Yermolenko et al., The Assembly of Nonadhesive Fibrinogen Matrices Depends on the aC Regions of the Fibrinogen Molecule, J. Biol. Chem, 287:41970-41990 (2012).

* cited by examiner

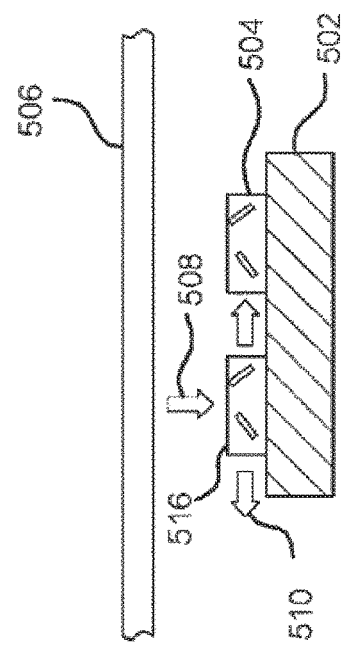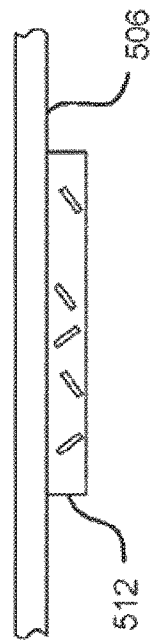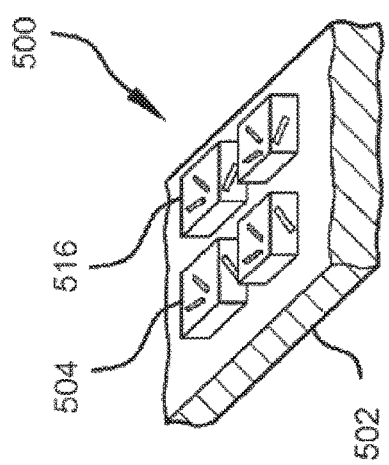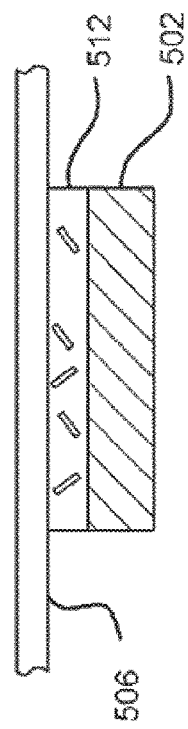

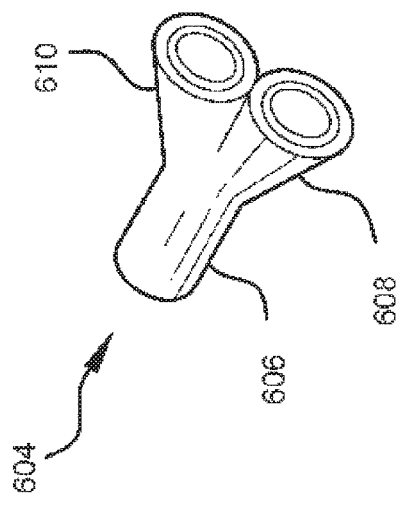
FIG. 6C
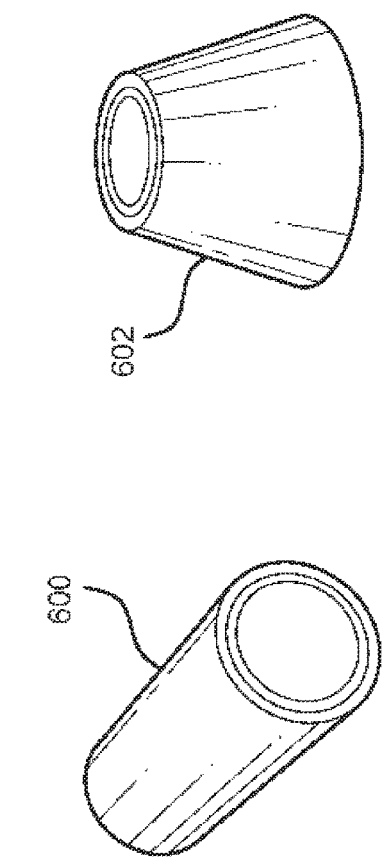
FIG. 6B
FIG. 6A
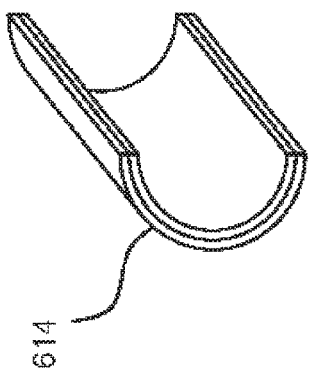
FIG. 6E
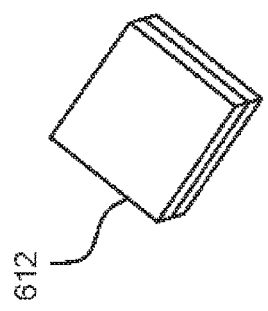
FIG. 6D

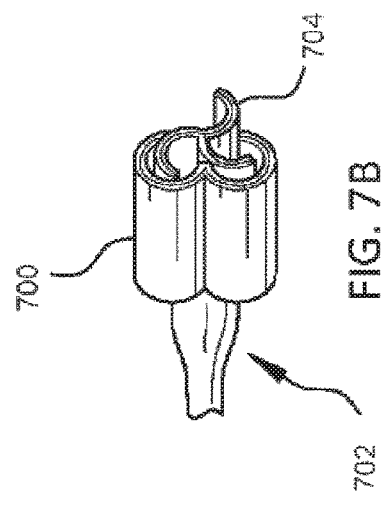
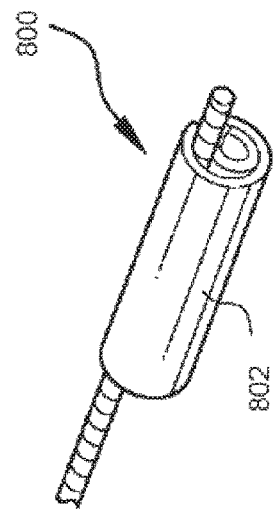
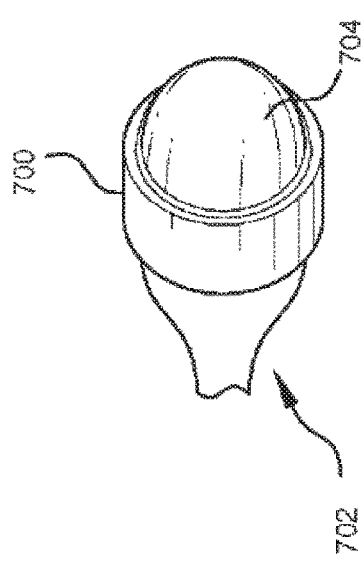
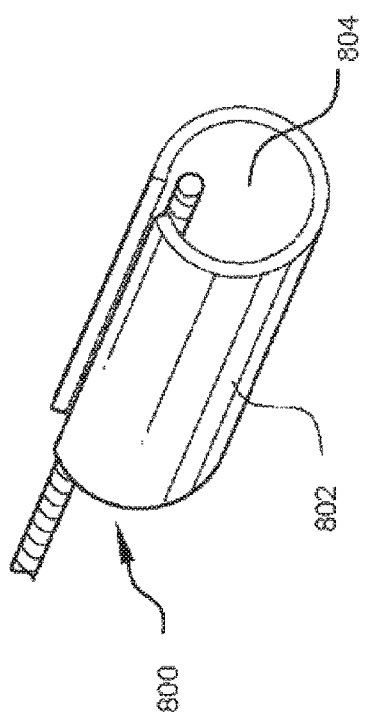

MULTI-LAYER BIODEGRADABLE DEVICE HAVING ADJUSTABLE DRUG RELEASE PROFILE

I. CROSS-REFERENCE TO RELATED APPLICATIONS

This application is a continuation patent application of U.S. patent application Ser. No. 15/046,285, filed Feb. 17, 2016, now U.S. Pat. No. 9,682,174, which is a divisional patent application of U.S. patent application Ser. No. 13/794,355, filed Mar. 11, 2013, now U.S. Pat. No. 9,271,925, the entire contents of each of which are incorporated hereby by reference.

II. FIELD OF THE INVENTION

The present invention relates generally to devices for drug delivery, including free-standing multi-layer biodegradable devices, especially useful in promoting healing of iatrogenic wounds and reducing the formation of post-operative lesions.

II. BACKGROUND OF THE INVENTION

Wounds to the human anatomy may result from interventional, minimally-invasive and/or intraoperative surgical procedures, acts, diseases, and/or underlying conditions. For example, iatrogenic wounds generally are formed during surgery for treating sinusitis, and due to the complicated topology of the sinuses, may take extended periods to heal. In addition, certain portions of the human anatomy are prone to the development of post-operative lesions, which often require treatment via subsequent surgical intervention.

Sinusitis is inflammation of the paranasal sinuses generally due to infection, allergies, or autoimmune issues. Chronic sinusitis affects persons of all age groups and is one of the more prevalent chronic diseases in the United States, affecting 37 million Americans. Chronic sinusitis may persist for 12 weeks or longer. Surgery, although minimally invasive, is generally reserved for acute/intermittent rhinosinusitis and chronic/persistent rhinosinusitis unresponsive to conservative medical treatment or where there are complications associated with those conditions. Functional endoscopic sinus surgery (FESS) of the diseased sinus mucosa has been proposed to enable ventilation through the natural ostia and restore mucociliary clearance using a minimally invasive endoscopic technique. Although FESS has proven to be an effective procedure in treating chronic sinusitis, the outcome of the surgery can become significantly complicated by operative pathologies, including delayed wound healing, stenosis of the sinus passageways (~in 20-30% of cases), adhesions, and the formation of polyps. Various mechanical means such as nasal stents and packings have been developed to treat such wounds; however, experience has shown that these methods do not provide an effective way of addressing the complications.

Pharmaceutical treatment of iatrogenic wounds with therapeutic agents such as steroids has been shown to reduce postoperative complications. However, there does not exist in the prior art an effective manner for delivering appropriate dosages of therapeutic agents over a desired timeframe within the sinus cavities.

Balloon sinus dilation is a relatively new technique for treating chronic sinusitis by opening blocked passages with balloon inflation. While more limited in application than FESS, this modality may become the treatment of choice for limited or moderate sinus disease. Accordingly, it would be desirable to provide an effective device for delivering a therapeutic agent to sinus tissue over a period of time following balloon sinus dilation.

U.S. patent application Publication Nos. 2011/0071498 and 2011/0071499 to Hakimimehr, assigned to the assignee of the present invention, the contents of both of which are hereby incorporated by reference, describe devices having a free-standing film of solid fibrinogen, and optionally solid thrombin, configured in the form a thin sheet. The device may be configured to release a therapeutic agent over time.

It would be desirable to provide a device, such as described in the foregoing Hakimimehr publications, that permits the release of different therapeutic agents over the same temporal profiles and/or different therapeutic agents over different temporal profiles.

III. SUMMARY OF THE INVENTION

In view of the foregoing, the present invention is directed to methods and apparatus for providing a biodegradable multi-layer device suitable for medical applications, especially treating, supporting, protecting or joining weakened tissue or vessels, and for promoting healing of same, resulting from iatrogenic causes, disease or underlying conditions. Advantageously, the multi-layer device of the present invention is formed from multiple film-layers having different characteristics from one another, e.g., configured to release the same or different therapeutic agents at the same or different release times, different adhesive properties, different stiffness properties, and/or different solubility properties.

In accordance with one aspect of the present invention, a device is provided comprising a first film-layer and a second film-layer bonded to the first film-layer. The first film-layer includes solid fibrinogen and is formed by processing (e.g., drying) a first composition for a first time interval to produce a first characteristic of the first film-layer. The second film-layer includes solid fibrinogen and is formed by processing (e.g., drying) a second composition for a second time interval to produce a second characteristic of the second film-layer. Preferably, the second characteristic is different than the first characteristic. As will be appreciated by one of ordinary skill in the art, while the device described herein is generally described as having two film-layers, a device constructed in accordance with the principles of the present invention may include any number of film-layers formed from multiple different compositions.

The first film-layer further may include a first therapeutic agent and the second film-layer further may include a second therapeutic agent which may be the same or different type or quantity as the first therapeutic agent. When the film-layers include a therapeutic agent, the first characteristic may be a first release profile for the first therapeutic agent and the second characteristic may be a second release profile for the second therapeutic agent. The first therapeutic agent or the second therapeutic agent or both may comprise one or more anti-inflammatory agents, anti-allergenic agents, anti-bacterial agents, anti-viral agents, anticholinergic agents, antihistamines, antithrombotic agents, anti-scarring agents, anti-proliferative agents, antihypertensive agents, anti-restenosis agents, healing promoting agents, vitamins, proteins, genes, growth factors, cells, RNA, or DNA.

In accordance with some aspects of the present invention, the first characteristic may be a first adhesive property of the first film-layer, a first solubility property of the first film-layer, a first surface roughness or texture property of the first film-layer, and/or a first stiffness property of the first film-layer. The second characteristic may be a second adhesive property of the second film-layer, a second solubility property of the second film-layer, a second surface roughness or texture property of the second film-layer, and/or a second stiffness property of the second film-layer. Advantageously, such first properties may be different from such second properties.

The first surface roughness or texture property of the first film-layer may include surface projections, perforations, microstructures, nanostructures, ridges, dimples, or any combination thereof and the second surface roughness or texture property of the second film-layer may include surface projections, perforations, microstructures, nanostructures, ridges, dimples, or any combination thereof.

The device may be configured to form a fibrin patch upon exposure to moisture (e.g., water, bodily fluids).

The first time interval for processing the first composition may be different from the second time interval for processing the second composition. In one embodiment, the first time interval is the amount of time required to substantially eliminate a first amount of non-aqueous solvent from the first composition and the second time interval is the amount of time required to substantially eliminate a second amount of non-aqueous solvent from the second composition. The first composition may be different than the second composition (e.g., different types of materials and/or different quantities of materials). The first composition may be bonded to the second composition before, during, or after the first and second film-layers are formed.

The solid fibrinogen of the first film-layer or the second film-layer or both may be prepared from unsalted fibrinogen. The first film-layer or the second film-layer or both further may include calcium salt, solid thrombin mixed with the solid fibrinogen, a plasticizer, a contrast agent that renders the device radiopaque, or any combination thereof.

The first film-layer or the second film-layer or both may include surface projections, perforations, microstructures, nanostructures, ridges, and/or dimples. The first film-layer or the second film-layer or both may be coated with, disposed between, and/or sandwich a protective layer. The device also may include an intermediate layer disposed between the first film-layer and the second film-layer. The intermediate layer may be configured to dissolve to create a reservoir, pores, void, or channel between the first film-layer and the second film-layer.

In accordance with one aspect of the present invention, a method of manufacturing a device is provided. The method includes forming a first film-layer from a first composition comprising solid fibrinogen and a first amount of non-aqueous solvent (e.g., ethanol) by processing (e.g., drying) the first composition for a first time interval required to substantially eliminate the first amount of non-aqueous solvent. The method further includes bonding a second film-layer to the first film-layer, wherein the second film-layer is formed from a second composition comprising solid fibrinogen and a second amount of non-aqueous solvent (e.g., ethanol) by processing (e.g., drying) the second composition for a second time interval required to substantially eliminate the second amount of non-aqueous solvent. The first time interval may be different from the second time interval.

Bonding the second film-layer to the first film-layer may include bonding the second film-layer to the first film-layer using an intermediate layer disposed between the first film-layer and the second film-layer. The intermediate layer may be configured to dissolve to leave a pore, a void, a reservoir, and/or a channel between the first film-layer and the second film-layer. Bonding the second film-layer to the first film-layer may occur before, during, or after forming the first film-layer and before, during, or after forming the second film-layer. Bonding the second film-layer to the first film-layer may include coupling the first film-layer to the second composition before forming the second film-layer. In addition, bonding the second film-layer to the first film-layer may include mechanically, chemically or electrically depositing, spraying, or casting the second film-layer on the first film-layer.

The first composition may be substantially identical to the second composition, except the first amount of non-aqueous solvent is different from the second amount of non-aqueous solvent. The first film-layer and the second film-layer have substantially identical optical characteristics.

In accordance with yet another aspect of the present invention, a method of delivering a device to a bodily tissue is provided. The method includes advancing a device comprising a first film-layer bonded to a second film-layer to a target location and applying the device to the bodily tissue. The first film-layer includes solid fibrinogen and is formed by processing a first composition for a first time interval to produce a first characteristic of the first film-layer. The second film-layer includes solid fibrinogen and is formed by processing a second composition for a second time interval to produce a second characteristic of the second film-layer. The second characteristic may be different than the first characteristic. The target location may include, but is not limited to, hollow body organs such the esophagus, stomach, intestines, bronchus, trachea, carina of the trachea, lung, larynx, urethra, ureter, the sinus, the ear, eye, or the heart; a lamina; vasculature such as a vessel; wound; tumor; or bone such as a spine Advancing the device may include advancing the device using a delivery system. Applying the device may include expanding an expandable member of the delivery system. The delivery system may have a protective sheath or protective outer or inner layer to prevent premature device placement or to prevent premature exposure of the first and second film layers to moisture before the device is applied to the bodily tissue. The device may be temporarily attached to the delivery system and may be releasable from the delivery system. The delivery system may be configured to conform the device to a three-dimensional shape and/or to the bodily tissue while applying the device to the bodily tissue. A component may be delivered to the device after application to the bodily tissue such that the component augments the device function by supplying the device with an activating agent or therapeutic agent. The device may also be applied to the bodily tissue using a trocar, tweezers, forceps, and/or clamps.

IV. BRIEF DESCRIPTION OF THE DRAWINGS

FIG. 1 is a schematic view of a first illustrative embodiment of a device of the present invention.

FIGS. 2A through 2C are schematic views of an alternative illustrative embodiment of a device of the present invention having an intermediate layer disposed between the first and second film-layers, wherein the intermediate layer is sandwiched between the film-layers in FIG. 2A, the intermediate layer is encased in the first and second film-layers in FIG. 2B, and FIG. 2C is a cross-sectional view of FIG. 2B.

FIGS. 5A-5D are, respectively, a schematic view of a further alternative embodiment of the device of present invention wherein discrete films of at least solid fibrinogen components are arranged on a protective layer, and illustrative views showing application of the device of FIG. 5A to a target location.

FIGS. 6A-6E are illustrative configurations for articles formed in accordance with the present invention.

FIGS. 7A and 7B illustrate one method by which a device of the present invention may be affixed to a balloon catheter.

FIGS. 8A and 8B illustrate an alternative balloon catheter that may be used to deliver the device of the present invention.

V. DETAILED DESCRIPTION OF THE INVENTION

The present invention is generally directed to a multi-layer biodegradable device for use in medical procedures for treating, healing, supporting, protecting or joining weakened or wounded tissue or vessels, resulting from interventional, minimally-invasive and intraoperative surgical procedures, disease, and/or underlying conditions. The multi-layer device of the present invention also may be used for isolating, occluding, supporting, and/or treating tissue, for example, as a drug delivery vehicle in the sinuses.

In accordance with one aspect of the invention, the multi-layer device may incorporate therapeutic agents such as drugs, genes or other bioactive agents that are eluted into the surrounding tissue to provide localized treatment or into an adjacent bloodstream to provide systemic treatment. Alternatively, such drugs, genes or other bioactive agents may be released into surrounding tissue or an adjacent bloodstream as the device biodegrades. Advantageously, the multi-layer device of the present invention is configured like the biodegradable devices of the aforementioned Hakimimehr applications with an improved multi-layer configuration whereby film-layers are formed with different characteristics, for example, to release different therapeutic agents at different release times or attain finer control of the therapeutic agent delivery rate.

The multi-layer device of the present invention also may include visible dyes or radiopaque materials to enhance visibility and placement of the device during deployment.

The multi-layer devices described herein may be delivered to a portion of the body using one or more delivery systems having one or more expandable members (e.g., an expandable cage, a balloon, and the like) and/or using a trocar, tweezers, forceps, clamps, or the like.

Multi-Layer Device Configurations

Multi-layer devices constructed in accordance with the principles of the present invention may be manufactured in either an adherent or non-adherent state. A multi-layer device also may be manufactured in a non-adherent state, and activated prior to use, for example, by dipping in warm water prior to application or delivery to the body. As yet another alternative, the multi-layer device may include a water-soluble protective coating, for example, for intravascular applications, to prevent the fibrin polymerization process from beginning before the device is delivered to a target location.

Figure 1:
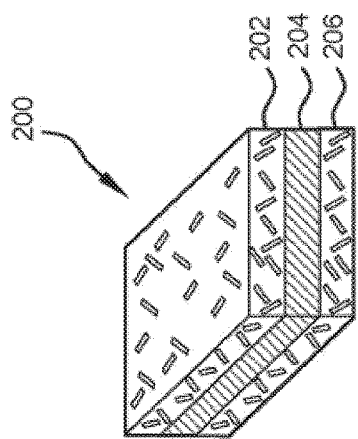

Referring now to FIG. 1, a first embodiment of a multi-layer device constructed in accordance with the principles of the present invention is described. Device 100 comprises first film-layer 102, which may be free-standing, having unreacted fibrinogen 104, and second film-layer 106, which may be free-standing, bonded to first film-layer 102, and having unreacted fibrinogen 104. First film-layer 102 and second film-layer 106 may include one or more additional components or agents, such as therapeutic agents, unreacted thrombin, calcium salt, Factor XIII, aprotinin, and/or other additives (e.g., plasticizers, stabilizers, dyes, radio-opacifiers, film-forming agents, and the like). Preferably, first film-layer 102 is processed in a manner to produce a first characteristic of first film-layer 102 and second film-layer 106 is processed in a manner to produce a second characteristic of second film-layer 106 different than the first characteristic. Examples of such characteristics include release profiles of therapeutic agents, adhesive properties, stiffness properties, and solubility properties.

First film-layer 102 may be formed from a first composition of materials that may include fibrinogen, thrombin, non-aqueous solvent(s), therapeutic agent(s), calcium salt, Factor XIII, aprotinin, and/or other additives (e.g., plasticizers, stabilizers, dyes, radio-opacifiers, film-forming agents, and the like). The first composition may be poured in a mold and processed for a first time interval, for example, the time required to substantially eliminate the amount of non-aqueous solvent in the first composition. The composition may be processed by, for example, drying including freeze-drying and vacuum-drying or incubating the composition. The first time interval may be predetermined by, for example, a technician or a computer or may be determined during a drying process by the technician using a computer that monitors the process or solely by the computer. The computer may be coupled to suitable sensors for determining when the amount of non-aqueous solvent is substantially eliminated. As will be readily understood by one of ordinary skill in the art, the term substantially as used herein means considerably or amply, e.g., greater than 50%, greater than 60%, greater than 70%, greater than 80%, greater than 90%, greater than 95%, greater than 99%.

Second film-layer 106 may be formed from a second composition of materials that may include fibrinogen, thrombin, non-aqueous solvent(s), therapeutic agent(s), calcium salt, Factor XIII, aprotinin, and/or other additives (e.g., plasticizers, stabilizers, dyes, radio-opacifiers, film-forming agents, and the like). The second composition may be the same as the first composition or may be different from the first composition e.g., different ratios of thrombin to fibrinogen, or different amounts of plasticizer, as required for a particular application such that the film-layers have different setting or degradation times, different stiffness, and/or release different drugs. The second composition may be poured in a mold and processed for a second time interval different from the first time interval, for example, the time required to substantially eliminate the amount of non-aqueous solvent in the second composition. This composition also may be processed by, for example, drying including freeze-drying and vacuum-drying or incubating the composition. This second time interval may be predetermined or determined during a drying process in the manner described above with respect to the first time interval.

The amount of time required to substantially eliminate the amount of non-aqueous solvent in a composition may be varied by varying the amount of non-aqueous solvent in the composition. Applicants have discovered that the amount of non-aqueous solvent in each composition has a significant impact on the characteristics (e.g., therapeutic release properties, adhesive properties, stiffness properties, solubility properties) of the film-layer that is formed from each respective composition. Applicants have further discovered that varying the amount of time required to substantially eliminate the amount of non-aqueous solvent by, for example, varying the air flow rates and/or humidity in the drying environment for each composition will also impact the characteristics of the film-layer that is formed from each respective composition.

In one embodiment, the time required to substantially eliminate the amount of non-aqueous solvent is varied by varying the humidity for different film-layers in a device that includes three film-layers. The middle film-layer of a multi-layer construct is configured for therapeutic agent delivery and is dried slowly in high humidity while the two outer films are dried significantly faster in lower humidity. In this embodiment, for example, the middle film-layer has a fibrinogen to non-aqueous solvent ratio of 1:100 (wt:wt) to 1:200 and is processed in an ambient humidity of 50-70%. The outer films have substantially lower fibrinogen to non-aqueous solvent ratio of less than 1:100 for example 1:40 and are processed in an ambient humidity of 10-50% or for example 20-40%. As a result, the middle film-layer of the device has different characteristic than the outer film-layers.

First film-layer 102 may include a first therapeutic agent while second film-layer 106 may include a second therapeutic agent which may be the same or a different type of therapeutic agent as the first therapeutic agent and may be provided in the same or different amount as the first therapeutic agent. Advantageously, first film-layer 102 has a first release profile, e.g., configured to release the first therapeutic agent over a first period of time, and second film-layer 106 has a second release profile, e.g., configured to release the second therapeutic agent over a second period of time, that may be different from the first release profile. The therapeutic agent release profile for each film-layer is directly impacted by the method of forming each film-layer.

Preferably, first film-layer 102 is bonded to second film-layer 106 and the bonding may occur before or after the film-layers are formed. For example, bonding first film-layer 102 to second-film layer 106 may include: (a) separately forming first film-layer 102 and second film-layer 106 and then bonding first film-layer 102 to second film-layer 106; (b) bonding first composition to second composition before first and second film-layers 102 and 106 are formed; (c) bonding first composition to second film-layer 106 before first film-layer 102 is formed; or (d) bonding second composition to first film-layer 102 before second film-layer 106 is formed. First film-layer 102 may be bonded to second film-layer 106 using one or more suitable biocompatible adhesives, a non-aqueous solvent such as ethanol, by pressing the film-layers together, or by painting, brushing, casting, or spraying one film-layer on another film-layer.

Device 100 may be configured to form a patch upon exposure to moisture. First film-layer 102 and second film-layer 106 include unreacted (e.g., solid) fibrinogen and optionally unreacted (e.g., solid) thrombin that may be polymerized to form a patch only after being exposed to moisture (e.g., water, bodily fluids such as blood, lymph, and mucous, and the like), preferably at the target location. When combined in a moist environment, thrombin converts fibrinogen into fibrin monomers, which are in turn polymerized to form fibers. These fibrin fibers join together into a network structure, resulting in a fibrin matrix. In an embodiment where the device does not include thrombin, device 100 may form a fibrin patch when fibrinogen in the film-layers reacts with naturally occurring thrombin in bodily fluids. The patch of the present invention may include one or more additional components, such as calcium, Factor XIII and bovine aprotinin, which may affect the rates of polymerization and biodegradation. Importantly, because fibrin is a part of the body's natural clotting mechanism, the in situ formed fibrin patches of the present invention are biocompatible, non-thrombogenic, biodegradable, and have a high affinity for various biological surfaces. In addition, because, in accordance with the present invention, the fibrinogen and thrombin may be combined in a non-aqueous environment, the components of the device do not polymerize to form a patch, e.g., a fibrin patch, until the device is exposed to an aqueous environment, such as bodily fluids.

As the polymerization process begins (e.g., when thrombin and fibrinogen are combined in the presence of moisture), the patch may temporarily become a gel and become highly adherent. Generally, it is expected that the patch may be freely manipulated, stretched, or deformed when in its temporary gel form. The duration of the gel stage may be dependent on the relative and overall concentrations of the fibrinogen and thrombin components, as well as the presence of any other components.

Figure 2A:
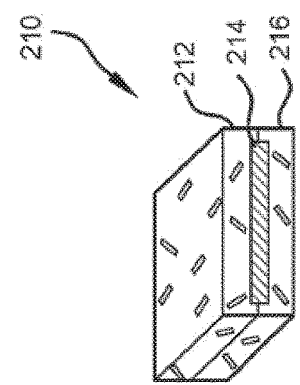
Figure 2B:
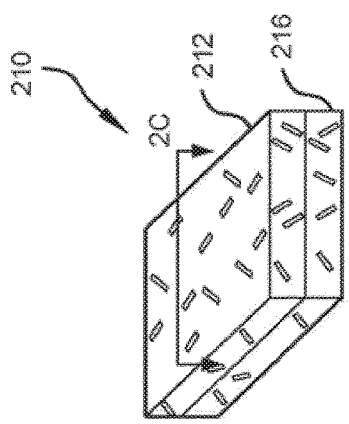
Figure 2C:
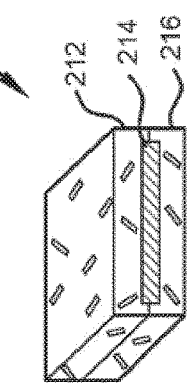

FIGS. 2A-2C illustrate an aspect the present invention, in which the device comprises an intermediate layer disposed between the film-layers. In FIG. 2A, device 200 comprises first film-layer 202, intermediate layer 204, and second film-layer 206. First and second film-layers 202 and 206 are similar to first and second film-layers 102 and 106, respectively, as described with respect to FIG. 1, and thus detailed descriptions thereof are omitted for clarity and conciseness. Illustratively, intermediate layer 204 is sandwiched between first film-layer 202 and second film-layer 206. In FIGS. 2B and 2C, device 210 comprises first film-layer 212, intermediate layer 214, and second film-layer 216. First and second film-layers 212 and 216 are similar to first and second film-layers 102 and 106, respectively, as described with respect to FIG. 1, and thus detailed descriptions thereof are omitted for clarity and conciseness. Illustratively, intermediate layer 214 is encased in first film-layer 202 and second film-layer 206.

Intermediate layer 204, 214 may be an adhesive configured to bond first film-layer 202, 212 to second film-layer 206, 216 and/or may comprise a water-soluble material, a material that is soluble in another media, a material that is electrolytically decomposable, a bioerodable or biodegradable material, e.g., biodegradable polymer, combinations thereof, or the like. Intermediate layer 204, 214 may be a continuous layer, a perforated layer, discrete formations, powder formations, or the like. In one embodiment, intermediate layer 204, 214 is configured to dissolve upon exposure to moisture to leave a pore(s), a void(s), a reservoir(s), and/or a channel(s) between first-film layer 202, 212 and second film-layer 206, 216. Such pore(s), a void(s), a reservoir(s), or a channel(s) permit fluid access within device 200, 210 and between first-film layer 202, 212 and second film-layer 206, 216. Such pore(s), a void(s), a reservoir(s), or a channel(s) also may act as actuators configured to collapse, swell, or otherwise mechanically change shape, to control mechanical aspects of device 200, 210 such as degradation rate or overall form factor or conformation of device 200, 210 and to allow for rapid release of therapeutic agent.

As will be readily apparent to one of ordinary skill in the art, first film-layer 202, 212, second film-layer 206, 216, and/or intermediate film layer 204, 214 may be separated by, disposed between, coupled to, and/or encased in a protective layer(s) such as the protective layer described below.

Figure 3B:
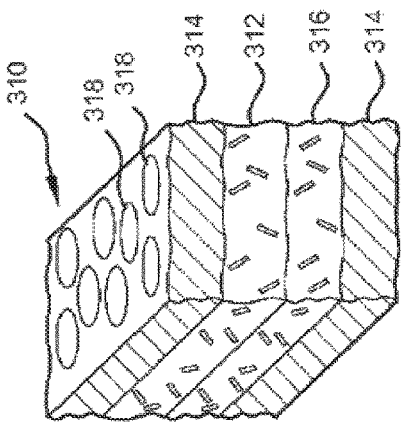
FIGS. 3A through 3C are schematic views of alternative illustrative embodiments of a device of the present invention in which two film-layers are sandwiched between protective layers in FIG. 3A, are sandwiched between perforated layers in FIG. 3B, or are coated with powder in FIG. 3C.
Figure 3A:
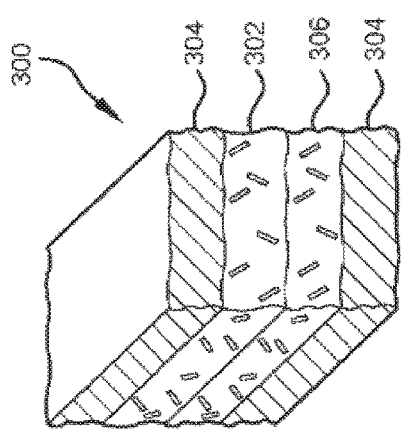

In FIG. 3A, device 300 is provided including first film-layer 302, protective layers 304, and second film-layer 306. First and second film-layers 302 and 306 are similar to first and second film-layers 102 and 106, respectively, as described with respect to FIG. 1, and thus detailed descriptions thereof are omitted for clarity and conciseness. Protective layer 304 may at least temporarily protect the film-layers from certain substances or stimuli prior to or during delivery, for example, exposure to moisture, to prevent premature activation. Alternatively, the protective layer may be selectively removed to control the activation of the device. In embodiments in which the device is already in an adherent form, a protective layer may help prevent premature adhesion between the device and surrounding tissue. In other instances, the protective layer may protect the device from mechanical damage prior to or during delivery. In still other embodiments, a protective layer may allow a device to be folded or otherwise manipulated (cut, rolled, bent, etc.) without adhering to itself. In yet other embodiments, a protective layer may be used to at least temporarily join a device to a delivery system, as described below.

In some embodiments, the protective layer may be removed from the device prior to or during delivery of the device. In this way, a device may be configured such that only the fibrin-forming layers (as well as an additives or therapeutic agents) are delivered to tissue. The protective layer may be made from a water-soluble material, a material that is soluble in another media, a material that is electrolytically decomposable, a bioerodable or biodegradable material, e.g., biodegradable polymer, combinations thereof, or the like. Examples of suitable water-soluble materials include, but are not limited to, polysaccharides (e.g., hyaluronic acid, cellulose, hydroxypropylmethyl cellulose, gelatin, starches, dextrans, alginates, their derivatives, and the like), contrast agents (e.g., diatrizoate, metrizoate, ioxaglate, iopamidol, iohexol, ioxilan, iopromide, iodixanol, and the like), sugar-based polymers (e.g., sucrose, dextrose), water-soluble hydrogels (polyethylene glycol, polyethylene oxide), combinations thereof, and the like.

While device 300 is depicted in FIG. 3A as having protective layers 304 on the outsides of film-layers 302 and 306, the device may include only one protective layer 304 attached thereto or a third protective layer between film-layers 302 and 306. Device 300 may also include a protective layer that encases, e.g., covers all of the exposed surfaces of, film-layers 302 and 306. As will be appreciated by one of ordinary skill in the art, while the device in this disclosure is generally described as having two film-layers, the device may include one, two, three, four, five, or more film-layers and may have one, two, three, four, five or more protective and/or intermediate layers without departing from the scope of this invention.

In FIG. 3B, device 310 is described that includes first film-layer 312, perforated layers 314, and second film-layer 316. First and second film-layers 312 and 316 are similar to first and second film-layers 102 and 106, respectively, as described with respect to FIG. 1, and thus detailed descriptions thereof are omitted for clarity and conciseness. Perforated layers 314 include a plurality of apertures 318 such that perforated layers 314 and first and second film-layers 312 and 316 may be exposed to moisture substantially simultaneously. Perforated layers 314 may be configured similar to intermediate layer 204, 214, protective layer 304, or may be formed from a composition of materials such as fibrinogen, thrombin, non-aqueous solvent(s), therapeutic agent(s), calcium salt, Factor XIII, aprotinin, and/or other additives (e.g., plasticizers, radio-opacifiers, film-forming agents, and the like).

Figure 3C:
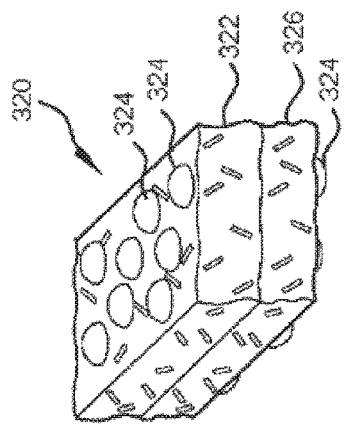

In FIG. 3C, device 320 is described that includes first film-layer 322, powder formations 324, and second film-layer 326. First and second film-layers 322 and 326 are similar to first and second film-layers 102 and 106, respectively, as described with respect to FIG. 1, and thus detailed descriptions thereof are omitted for clarity and conciseness. Powder formations 324 are powder and are coupled to the film-layers using a suitable technique such as spray coating. Powder formations 324 need not fully cover first and second film-layers 312 and 316 such that the film-layers and the powder may be exposed to moisture substantially simultaneously. Powder formations 324 may be configured similar to intermediate layer 204, 214, protective layer 304, or may be formed from a composition of materials such as fibrinogen, thrombin, non-aqueous solvent(s), therapeutic agent(s), calcium salt, Factor XIII, aprotinin, and/or other additives (e.g., plasticizers, radio-opacifiers, film-forming agents, and the like). Preferably, powder formations 324 comprise solid fibrinogen or a powder mixture of solid fibrinogen and solid thrombin.

Figure 4:
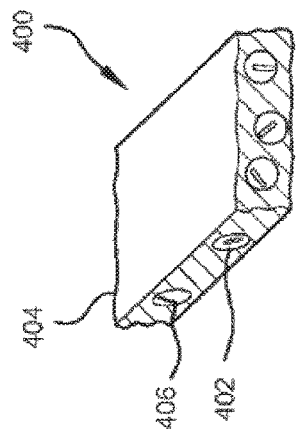
FIG. 4 is a schematic view of another alternative illustrative embodiment of a device of the present invention wherein discrete segments of solid fibrinogen components are embedded in a water-soluble protective layer.

Referring to FIG. 4, a further alternative of a device constructed in accordance with the principles of the invention is described. Device 400 comprises discrete or interconnected portions or strands 402 and 406 of solid unreacted fibrinogen disposed within matrix 404. Matrix 404 may be configured similar to intermediate layer 204, 214, protective layer 304, or may be formed from a composition of materials such as fibrinogen, thrombin, non-aqueous solvent(s), therapeutic agent(s), calcium salt, Factor XIII, aprotinin, and/or other additives (e.g., plasticizers, radio-opacifiers, film-forming agents, and the like). In some of these variations, matrix 404 may protect components 402 and 406 from premature activation. Additionally, matrix 404 may provide device 400 with additional flexibility or rigidity, as may be desired for a particular application. In one embodiment, component 402 is formed in a manner similar to first film-layer 102 of FIG. 1 and fibrin-forming component 406 is formed in a manner similar to second film-layer 106 of FIG. 1 such that components 402 and 406 have at least one different characteristic from one another.

In one embodiment, components 402 and 406 include a mixture of unreacted fibrinogen and unreacted thrombin. In this embodiment, when device 400 is delivered, e.g., into a sinus of a patient, the solid unreacted fibrinogen and thrombin portions 402 and 406 may adhere to tissue. However, matrix 404, which may be a water-soluble material, initially protects the fibrin-forming components from polymerizing. As water-soluble matrix 404 dissolves during exposure within the body, portions 402 and 406 are exposed, thereby initiating polymerization. Such exposure also may allow the device to form fibrin gel to adhere to the bodily tissue and cure to form a fibrin-matrix patch. Pressure applied by a delivery device (e.g., by an inflated balloon), may cause portions 402 and 406 to join and form a continuous film-layer within the body. In other embodiments, matrix 404 may be a biodegradable material, such that exposed portions of the unreacted fibrin-forming components 402 and 406 become adherent, thereby allowing device 400, including biodegradable matrix 404, to form a patch(es) and adhere to surrounding tissue.

In other variations, a multi-layer device of the present invention may be formed with the unreacted fibrinogen arranged in predetermined patterns. For example, in some variations, the components, e.g., film-layers, may be arranged in a mesh-like pattern. In still other variations, the components may be divided into a plurality of discrete segments. FIGS. 5A-5D illustrate one such variation, device 500. FIG. 5A is a perspective view of device 500, which includes film-layers 504 (similar to first film-layer 102 of FIG. 1) and film-layers 516 (similar to second film-layer 106 of FIG. 1) deposited on protective layer 502 (similar to protective layer 304 of FIG. 3A). While shown in FIG. 5A as having protective layer 502, it should be appreciated that film-layers 504 and 516 alternatively may be deposited directly onto one or more portions of a delivery device, with or without a protective layer. An additional protective layer(s) (not shown) may be used to cover some or all of the film-layers during delivery.

As illustrated in FIGS. 5B through 5D, although film-layers 504 and 516 may be divided into a number of discrete segments, some or all of the film-layers 504 and 516 may be joined in situ to form a continuous film. More specifically, in embodiments in which film-layers 504 and 516 take on a gel form after activation, the segments may be manipulated or remodeled by the application of one or more forces. For example, when device 500 described above is pressed against sinus wall 506 by an expandable delivery device (not shown), the device and sinus wall may apply pressure (indicated by the arrows in FIG. 5B) to film-layers 504 and 516 that cause the gelatinous, partially-cured film-layers 504 and 516 to deform outwardly, as shown by arrows 510. This deformation may in turn cause individual film-layers 504 and 516 to join into solid film 512, as depicted in FIG. 5C. Protective layer 502 may thereafter be removed or dissolve, as shown in FIG. 5D.

Dividing the unreacted fibrinogen components into discrete film-layers 504 and 516 may provide a number of advantages. For example, a device made up of discrete film-layers 504 and 516 may have additional flexibility compared to a solid continuous layer, thereby enabling the device to be folded to facilitate transluminal delivery. In other instances, discrete film-layers 504 and 516 may be used to form a continuous film that will not block a side branch when deployed in a branched blood vessel. In such cases, it is expected that only those film-layers 504 and 516 that contact a tissue surface will deform, and thus film-layers 504 and 516 that do not contact tissue will not contribute to forming a continuous film. As such, if a balloon carrying discrete film-layers 504 and 516 is expanded inside of a branched vessel; those segments that are expanded toward the side branch will not contact tissue.

A multi-layer device of the present invention may have any suitable size and shape, such that the dimensions of the device may be determined at least in part by the dimensions of the anatomy in which the device will be applied. In addition, devices of unreacted fibrinogen or thrombin, with or without additional additives as described above, may be modeled into any suitable size of shape, depending upon the intended application. FIGS. 6A-6E illustrate a number of devices with multiple film-layers and articles modeled from such devices. For example, FIG. 6A illustrates device 600 having the form of a hollow cylinder, and may find particular utility where the device will be placed in a cylindrical hollow body organ. Device 602 of FIG. B illustrates that a device of the present invention may take on any other three-dimensional shape, such as a frustroconical section.

Other suitable three-dimensional shapes may include, but are not limited to, spheres, hemispheres and cones. In FIG. 6C, device 604 is configured as a branched cylinder having main trunk 606 and first 608 and second 610 side branches, such as may be required to provide internal or external support for a branched vessel. While shown in FIG. 6C as having a generally y-shaped configuration, device 604 may be configured such that side branches 608 and 610 project from main trunk 606 at any desired point along the length of main trunk 606.

In other embodiments, a device constructed in accordance with the principles of the present invention may be formed in a flat shape, such as device 612 of FIG. 6D. While shown in FIG. 6D as being approximately rectangular in shape, device 612 may be any suitable shape, including, but not limited to, a circle, an oval, a triangle, a square, another polygon, or a shape with irregular geometry. Additionally, device 612 may be rolled, folded, bent or otherwise modified to form a three-dimensional shape. For example, FIG. 6E shows rectangular device 614 that has been curved to form a half-cylinder, e.g., to mate with an interior surface of a vessel to occlude or isolate an aneurysm. In other variations, the shape of the device may be dependent on the system that will deliver it. For example, a device, according to the present invention, may be formed by depositing a film-layer of unreacted fibrinogen and thrombin, or just unreacted fibrinogen, with or without a salt component, on a portion of the delivery system (e.g., a balloon). In such instances, the shape of the device will be the same or similar to the shape of delivery system.

It should be appreciated that the shape and dimensions of a device may change before or during delivery of the device and before or after formation of the patch. For example, the device may be folded, crimped, stretched or otherwise deformed in a manner that modifies, temporarily or permanently, the shape of the device. Furthermore, the ultimate size and shape of the in situ device formed within the body may differ from the shape of the device as manufactured. Due to the deformability of the fibrinogen and thrombin components during polymerization, some devices may be molded or otherwise deformed during delivery. For example, in variations where a cylindrical device is delivered using a balloon, inflation of the balloon may cause the device to expand to a larger radius.

The device may also incorporate specific features to allow for accelerated tissue healing or improved therapeutic benefit. Features such as perforations in a single layer or through the device and through all layers may allow for more rapid tissue in growth or discrete exposure of underlying layers within the device to the tissue surface. The device also may include specific surface architectures or structures such as projections, ridges, dimples, or micro or nanostructures that enhance bonding and/or improve penetration of therapeutic agents into the tissue. Such surface architectures or structures may be on the entire device, or on individual or multiple layers including a film-layer, an intermediate layer, and/or a protective layer.

Delivery Systems and Methods

The multi-layer devices described herein may be delivered using of a number of previously-known delivery systems, which may comprise, for example, one or more expandable members, such as a balloon or expanding mandrel or cage. In embodiments that include an expandable member, the expandable member may be expanded at the delivery site to position a device so that it is in apposition with tissue and to expose the device to moisture at the tissue, to optionally form a patch. In instances where a device is placed in a dry environment, or when the delivery system is used to deliver a liquid component, the delivery system may additionally include one or more lines, lumens, ports or the like for delivering water or a liquid component to the device to expose the device to moisture.

As explained above, the multi-layer devices may be configured to contain pore(s), a void(s), a reservoir(s), and/or a channel(s), e.g., after dissolution of an intermediate layer. In one embodiment, such pore(s), a void(s), a reservoir(s), and/or a channel(s) may be expanded and/or accessed by the delivery system. In such an embodiment, the delivery system includes a needle(s), line(s), lumen(s), and/or port(s) configured to deliver a fluid, therapeutic agent, and/or activating agent to the pore(s), a void(s), a reservoir(s), and/or a channel(s) after in vivo implantation of the device.

In instances where the device is delivered using a balloon catheter, the balloon may be compliant, semi-compliant, or non-compliant. When a balloon catheter is used to deliver a multi-layer device of the present invention, the device may first be placed on or otherwise attached to the balloon. In some variations, a device may be mechanically attached to the balloon. Alternatively, one or more clips, sutures, magnets, coatings or other mechanical structures may be used to hold the device to the balloon. In variations where a non-or semi-compliant balloon is either folded or rolled, the folding or rolling of the balloon may hold the device against or to the balloon. FIGS. 7A and 7B illustrate one manner by which a device may be folded with a non-compliant or semi-compliant balloon to mechanically hold the device on the balloon. In particular, FIG. 7A depicts cylindrical device 700 (similar to device 100 of FIG. 1) and balloon catheter 702 comprising balloon 704. As shown in FIG. 7A, balloon 704 has been placed inside of the device 700 and inflated. To hold device 700, balloon 704 may be deflated and folded. During this process, device 700 becomes folded along with the non-compliant balloon, as shown in FIG. 7B, such that the resulting folds of balloon 704 temporarily hold device 700 on the balloon. Device 700 is released when balloon 704 is later re-inflated and may be activated to form a patch upon exposure to moisture.

In other embodiments, the device may be temporarily attached to the balloon using one or more adhesives, which may be water-soluble and release the device when exposed to water. For example, in some variations a water-soluble protective layer may be used to join a device to a delivery system and later release the device from the delivery system. In other variations, the adhesive may lose its grip on the balloon in response to one or more stimuli (e.g., chemical, electrical, thermal, optical, mechanical) which may be applied to the balloon catheter to release the device in situ.

In still other embodiments, the unreacted fibrinogen and/or thrombin components of the device may be deposited directly onto the balloon of a delivery catheter using any suitable deposition process. Examples of suitable deposition methods include, but are not limited to, spray coating, electrodepositing, dip coating, brushing, rolling, spinning, inkjet printing, casting or the like. Where the device comprises multiple layers (e.g., film-layers, protective layers, intermediate layers, and adhesive layers), each layer may be applied sequentially, and may be applied using the same or different deposition methods. For example, a balloon may first be coated with a protective layer, a layer of unreacted fibrinogen and thrombin then applied, and finally the assembly may be coated with an additional protective layer, such as a water-soluble layer. When multiple discrete segments are used to create the device, such as described with respect to device 500 of FIG. 5A, film-layers 504 and 516 may be applied simultaneously or sequentially. Additionally, the final layer of protective coating also may serve to secure the device to the balloon.

When the fibrin-forming components are used to at least partially coat a balloon, the balloon may be either deflated or inflated when coated. For example, in some variations an inflated non-compliant or semicompliant balloon may be coated with a device, deflated, and then rolled or folded with the solid device attached thereto. In other instances, a deflated non-compliant or semicompliant balloon may be rolled or folded, and then coated with a device. Compliant balloons may be coated when they are at least partially deflated. Additionally, the balloon of a balloon catheter may be made from or coated with a non-adhesive material, such as PTFE. In this case, the non-adhesive material may help to prevent the device from adhering to the balloon during delivery. The balloon of the delivery catheter optionally may be textured, dimpled, or otherwise patterned to allow for temporary mechanical adherence between the balloon and the device.

Referring now to FIGS. 8A and 8B, an alternative delivery system suitable for delivering a multi-layer device of the present invention is described. Balloon catheter 800 includes curved, rectangular balloon 802 that approximates a cylindrical shape when inflated. When deflated, balloon 802 may be folded or rolled into a spiral, as shown in a FIG. 8B. Because balloon 802 may be laid flat when deflated, balloon catheter 800 may find particular utility in instances where a device (not shown) is deposited directly on balloon 802, for example, by casting, spraying or using an inkjet printing method. Additionally, because balloon 802 approximates a cylindrical shape when inflated, blood may still pass through lumen 804 defined by balloon 802 during deployment, thereby reducing the risk of upstream ischemia during placement of the device and optional activation of the patch.

Delivery systems suitable for delivering the multi-layer device of the present invention may additionally comprise one or more protective sheaths. Generally, an expandable member may be placed in a low-profile configuration inside of a sheath, and advanced to a target site. At the target site, the sheath may be withdrawn (or the expandable member advanced) to reveal the expandable member. In this way, the sheath may help to shield the device from exposure to moisture or other stimuli as the device is advanced through the body. One such delivery system is depicted in FIGS. 9A-9E. Alternatively, the sheath may have a diameter that varies along the length of the catheter, e.g., having a smaller diameter on the shaft and an enlarged diameter in the vicinity of the balloon, so that the sheath does not reduce flexibility of the delivery system.

Figure 9C:
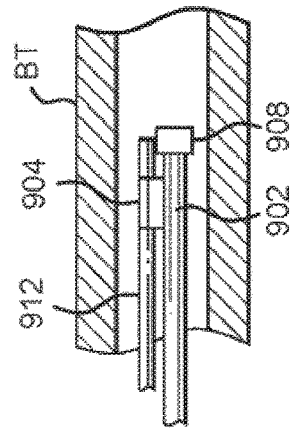
FIGS. 9A-9E illustrate a method of deploying the device of the present invention on bodily tissue.
Figure 9E:
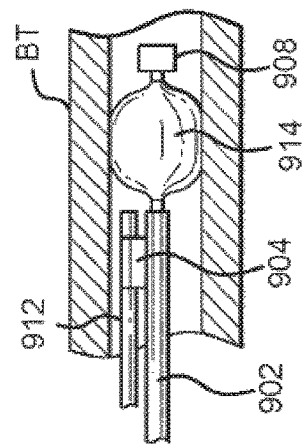
Figure 9B:
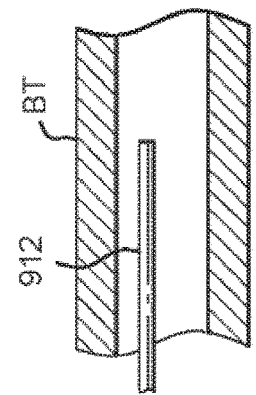
Figure 9D:
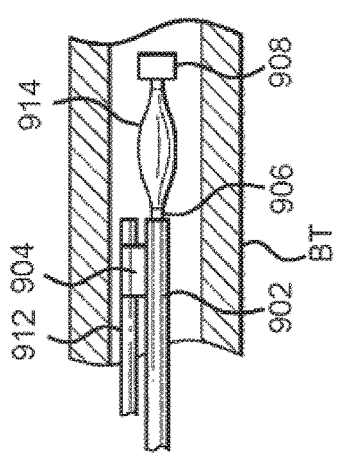
Figure 9A:
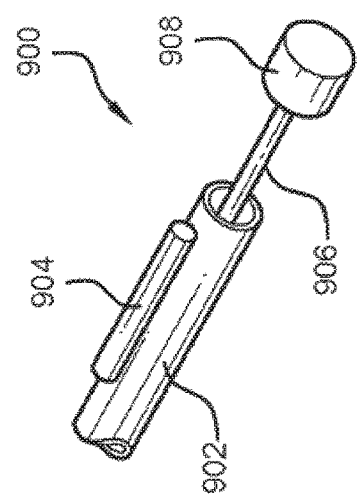

In FIGS. 9A to 9E, delivery system 900 comprises sheath 902, collar 904 disposed on sheath 902, and shaft 906 with cap 908. Cap 908 may be configured to engage the distal end of sheath 902 to seal the interior of sheath 902 from the external environment during advancement of the delivery system through a patient's anatomy. Shaft 906 may be slidable relative to sheath 902 to move cap 908. To deliver a device within bodily tissue BT, guidewire 912 is first advanced to a target site, as shown in FIG. 9B. Sheath 902 then is advanced along guidewire 912 via collar 904, as depicted in FIG. 9C. While shown in FIGS. 9A-9E as having a collar, delivery system 900 need not include such structure, but instead may employ any other structure used for advancing a catheter. Once sheath 902 has been advanced to the target site, shaft 906 is advanced relative to sheath 902 to expose balloon 914 (or another expandable member), as shown in FIG. 9D. Balloon 914 then is expanded to bring the device (not shown) into apposition with the interior of bodily tissue BT. Balloon 914 may be retained in position for a sufficient period of time for the patch to activate and adhere to the bodily tissue wall, e.g., 30 seconds to several minutes. Balloon 914 then is deflated and delivery system 900 removed.

The multi-layer device of the present invention may be delivered using any suitable delivery system, such as those described above. The delivery system may comprise a sheath, which may or may not be steerable. Advancement of the delivery system and deployment of the device may occur under direct visualization, indirect visualization, or a combination thereof. In variations where the delivery system is advanced using indirect visualization, any suitable visualization technique may be used (i.e., fluoroscopy, ultrasound), and either the delivery system or the adhesive may include one or more radiographic components to help aid in visualization.

In accordance with the present invention, the multi-layer device may be advanced to a target location and applied to bodily tissue using a trocar, tweezers, forceps, clamps, or the like and techniques known in the art.

Multi-layer devices constructed in accordance with the present invention may be delivered to any suitable target location of the anatomy. For example, one or more devices may be delivered to one or more hollow body organs, such as the esophagus, stomach, intestines, bronchus, trachea, lungs, urethra, ureters, the sinuses, the ears, eyes, or the heart and optionally exposed to moisture at bodily tissue, e.g., the wall of the organ. In embodiments configured for use in a heart, the device may be used to treat or seal a patent foramen ovale, a paravalvular leak, the left auricular appendage, or the like. In other embodiments, the inventive devices may be used to modify the geometry of the left ventricle, and thus reduce functional mitral regurgitation.

Multi-layer devices constructed in accordance with the present invention may be delivered to target locations that include wounds resulting from interventional, minimally-invasive and/or intraoperative surgical procedures, diseases, and/or underlying conditions.

In one proposed application, a device of the present invention is advanced to a target location in the sinuses and applied to bodily tissue within the sinus to treat iatrogenic wounds resulting from surgical procedures for treating, for example, sinusitis. The device may be applied to areas such as, but not limited to, a paranasal sinus, ethmoid sinus, ethmoidotomy channel, and frontal sinus outflow tract. A device of the present invention may also be delivered by a delivery system, such as the delivery system described above, having an expandable member (e.g., a balloon, cage, or other expandable structure) or using a sinus insertion device such as a flexible delivery cannula to the osteomeatal complex, along the maxillary ostium or any sinus insertion device capable of accessing the maxillary ostium.

A multi-layer device constructed in accordance with the present invention provides many advantages for treating wounds, such as iatrogenic wounds resulting from surgical procedures for treating sinusitis. One advantage is that a therapeutic agent, such as a steroidal anti-inflammatory agent, may be delivered locally with minimal systemic exposure to significantly improve the outcome of surgery. Another advantage is that the device naturally biodegrades so there is no need for subsequent removal. A further advantage is that the device improves the healing of the mucosal lining so as to reduce healing time, and thus, reduce the likelihood of the formation of adhesions. Yet another advantage is that the device is configured to seal the mucosal wall, which may prevent adhesions of the opposing surfaces in the sinuses. Another advantage is that the device adheres to the sinus wall of the nasal passageway in a thin layer and therefore does not obstruct the flow of air and liquid; thereby improving the quality of life after surgery. Yet a further advantage is that because the device adheres to the sinus wall, rather than being retained in position by mechanical force from, for example, a stent, further damage to the mucosal layer is prevented, which in turn leads to improved quality of life.

In another proposed application, a device of the present invention is advanced to a target location in the bronchus and applied to bodily tissue at an anastomosis site within the bronchus to treat post-operative lesions following a surgical procedure, such as lung transplantation. Bronchial stenosis following lung transplantation is such a problem, often arising from scar stenosis at the bronchial anastomotic site with or without previous anastomotic dehiscence. The device of the present invention may be delivered to the anastomosis site using a suitable delivery system and applied to bodily tissue using the adhesive properties of the device. The device may release therapeutic agent(s) such as cyclosporine or another antiproliferative agents that promote healing while the device biodegrades. The device may be applied to bodily tissue surgically or during an anastomosis procedure.

In a further proposed application, a device of the present invention is advanced to a target location in the larynx, trachea, carina, or bronchi and applied to bodily tissue at a stenosed area within the larynx, trachea, carina, or bronchi to treat post-operative lesions resulting from surgical procedures for treating, for example, airway stenosis, such as post-intubation tracheal stenosis. The device of the present invention may be delivered to the affected area using a suitable delivery system, e.g., in conjunction with balloon dilation opening the restricted passageway. After application, the device may release therapeutic agent(s) such as antiproliferative agents and/or anti-inflammatory agents to the affected site to improve the outcome of the balloon dilation.

In yet another proposed application, a device of the present invention is advanced to a target location in a neck in a lobe of the lung and applied to bodily tissue at the wall of the lobe to treat wounds from, for example, asthma. The device may release therapeutic agent(s) such as steroidal anti-inflammatory agents to the lungs. The device is believed to minimize the systemic exposure to steroids and to improve patient compliance.

In another proposed application, a device of the present invention is advanced to a target location in the trachea or bronchi and applied to bodily tissue at a ulcer at the trachea or bronchi to treat lesions resulting from tumors, for example, squamous cell carcinomas. The device may be used to aid in the treatment of bronchial tumor resection or weakened bronchia due to external beam radiation therapy. The device may release therapeutic agent(s) such as chemotherapeutics (e.g., antiproliferative agents or antibody based therapies), anti-inflammatory agents, and/or antibiotics to the bodily tissue. The device may be delivered after open surgery or during an endoscopic procedure such as a bronchoscopy.

In yet another proposed application, a device of the present invention is advanced to a target location in the body and applied to bodily tissue at an internal adhesion or (potential) dermal scar to treat lesions resulting from, for example, invasive surgical procedures. The device may be used in preventing or reducing the size of internal adhesions or dermal scarring. An adhesion is a band of scar tissue that binds together two internal body surfaces. Adhesions can cause subsequent health issues such as pain (back and abdominal), infertility, and digestive issues resulting in increased costs and potential secondary surgical interventions. The device of the present invention may act as a barrier between two body surfaces during the healing process; it then biodegrades and provides a space between the two surfaces. The device also may release therapeutic agent(s) such as anti-inflammatory agents, antiproliferative agents, antibiotics, and/or mitomycin C to promote healing of an adhesion or scar.

In another proposed application, a device of the present invention is advanced to a target location in or on the body and applied to bodily tissue to promote healing. The device may release therapeutic agent(s) such as antibiotic agents, antimicrobial agents, antifungal agents, growth factors, and/or analgesic agents to promote wound healing. For example, a device for treating diabetic ulcers may release an antibiotic agent. Advantageously, since the device is biodegradable, it does not need to be removed before a new dressing is put in place and therefore prevents interruption of wound healing due to change of dressing.

In a further proposed application, a device of the present invention is advanced to a target location in or on the body and applied to bodily tissue at a site of pain to treat pain and/or inflammation. For example, the device may be used to treat radicular pain and sciatica of the lower back or articular pain of the joint. The device may be advanced to a target location at a joint or a space inside the body using a trocar delivery device. In one embodiment, the device is inserted minimally invasively via epidural trocar into the foraminal or interlaminar space of the lumbar spine. Preferably, the device is configured to release therapeutic agent(s) such as anti-inflammatory agents, analgesic agents, anti-infective agents, and/or anti-proliferative agents. As described throughout this disclosure, the device may contain multiple film-layers for the programmed release of different therapeutic agents with different temporal profiles. For example, acute analgesics such as the-caine derivatives may be delivered immediately and over a duration of up to the first 8-12 hours, while an anti-inflammatory agent may be delivered for a much longer period. In another embodiment, the device may be applied after an open or minimally invasive surgery (laparoscopic surgery) to deliver therapeutic agents to improve the outcome of the surgery. For example, a device with a steroidal anti-inflammatory agent may be applied after a laparoscopic spinal surgery to reduce inflammation and pain after surgery. In addition, therapeutic agent(s) for promoting wound healing may alleviate the side effects of epidural steroid injections such as dural puncture and prevent cerebral spinal fluid leakage.

In yet another proposed application, a device of the present invention is advanced to a target location in the eye and applied to bodily tissue within or on the eye. In one embodiment, the device may be applied to the posterior segment of the eye via the vitreous or suprachoroidal space using a cannula, e.g., a 20 to 25 gauge cannula. The device also may be applied after vitreoretinal surgery to release a therapeutic agent(s) such as an anti-inflammatory agent over a period of time. The device may biodegrade slowly over time thus obviating the need for subsequent surgical extraction and may deliver a sustained profile of therapeutic agent. The adhesive properties of the device allow it to be applied in contact with and adhering to the macular surface within the eye so as to avoid visual problems associated with an untethered device in the vitreous.

In another proposed application, a device of the present invention is advanced to a target location that is a tumor anywhere in or on the body and applied to bodily tissue at the tumor as a primary mode of treatment or in conjunction with surgery or a minimally invasive surgery as a maintenance therapy to prevent tumor re-growth. The device may release therapeutic agent(s) such as chemotherapeutics including anti-proliferative agents to the site of the tumor. Examples for this application include delivering the device using a non-invasive delivery system such as a balloon catheter to a tumor of the bladder; delivering anti-cancer therapeutics to a tumor of the airway using a balloon catheter; and delivering the device having an anti-cancer agent surgically to a resected tumor of the pancreas.

In yet another proposed application, a device of the present invention is advanced to a target location in the heart or in a blood vessel and applied to bodily tissue at a wall of the heart or vessel to treat wounds from, for example, cardiac disease or surgical procedures for treating cardiac disease.

Additionally, the device of the present invention may promote endothelialization by delivery of growth factors. In still other instances, one or more devices may be used to attach endothelial cells to the inside of the lumen to promote healing. In yet another proposed application, a device of the present invention may be delivered, e.g., using a bronchoscope balloon, within a patient's bronchus or trachea to deliver chemotherapy or an anti-cancer drug through the patient's vasculature or tissue.

Device Composition

As described above, first, second, third, fourth, fifth, or more compositions may be used to form first, second, third, fourth, fifth, or more film-layers that form a multi-layer device when exposed to moisture. The compositions and film-layers may comprise fibrinogen, thrombin, therapeutic agent(s), calcium salt, Factor XIII, aprotinin, and/or other additives (e.g., plasticizers, stabilizers, dyes, radio-opacifiers, film-forming agents, and the like) and the compositions may further include non-aqueous solvent(s) such as ethanol. The compositions of the device may be tailored to achieve various characteristics including a preferred setting time, matrix stiffness, porosity, and degradation rate, depending upon the intended application. The fibrinogen and, if present, thrombin components may be deposited on a surface via spray coating, dip coating, brushing, rolling, spinning, electrospraying, casting, inkjet printing, or the like.

The compositions, and thus the film-layers, described above may further include an antifibrinolytic agent or antiplasmin agent to prolong the biodegradation timeline of the device. Examples of antifibrinolytic agents include, but are not limited to, aprotinin, tranexamic acid, and aminocaproic acid.

It is expected that commercially available fibrinogen products may be used to prepare a device in accordance with the present invention. Also, commercially available purified human fibrinogen products prepared without any excipients or stabilizers, such as sodium citrate or sodium chloride, may be used. One commercially available fibrinogen product that has been used is Part No. PP001S, available from Hyphen Biomed, Neuville-sur-Oise, France, distributed in the United States by Aniara Corporation, Mason, Ohio.

A device in accordance with the present invention may comprise a layer of solid fibrinogen, that may be unsalted, as described above. Fibrinogen-only or fibrinogen plus calcium salt devices are expected to have different mechanical properties when delivered to tissue compared to devices that contain thrombin. As explained earlier, however, the addition and amount of calcium salt may be tailored to obtain specific mechanical properties for a device, as may be suitable for particular applications.

It is expected that commercially available thrombin also may be used to prepare a device in accordance with the present invention. Initial tests conducted with human thrombin, Part No. AEZ0060, available from Hyphen Biomed, Neuville-sur-Oise, France, distributed in the United States by Aniara Corporation, Mason, Ohio, have produced satisfactory results. In addition, the presence of some excipients in commercial sources of thrombin have not been observed to effect the mechanical characteristics of the device.

A device constructed in accordance with the principles of the present invention may comprise one or more plasticizers that may increase the flexibility of the device, improving the device integrity and making it less prone to cracking or flaking. Examples of suitable plasticizers include, but are not limited to, PEG-6000, PEG-3000, PEG-1500, PEG-400, glycerol, and polyvinyl, phthalate esters (e.g., diethyl phthalate), sebacate esters (e.g., dibutyl sebacate), citrate esters (e.g., triethyl citrate, tributyl citrate), glycerol derivatives (e.g., propylene glycol, poly(ethylene glycol) which may be about 1 to about 90 weight percent polyethelene glycol, about 5 to about 75 weight percent polyethelene glycol, about 5 to about 60 weight percent polyethelene glycol, about 5 to about 50 weight percent polyethelene glycol, about 5 to about 40 weight percent polyethelene glycol, or about 5 to about 30 weight percent polyethelene glycol), surfactants, preservatives, combinations thereof, and the like. The amount of plasticizer may vary depending on the intended application as well as the desired flexibility for the device, and generally will comprise less than about 50% of the constituents used to prepare the device.

In other embodiments, a device may comprise one or more radio-opacifier substances that allow the device to be imaged fluoroscopically prior to, during, or after implantation. Examples of suitable radio-opacifiers include, but are not limited to, materials containing bismuth, barium (e.g., barium sulphate), gold, iodine, platinum, or tantalum, zirconium oxide and iron oxide. In some embodiments described below, the radio-opacifier may be provided in high concentrations in only discrete areas of the device.

The device of the present invention optionally may incorporate one or more film-forming agents. Generally, a film-forming agent may assist in forming a continuous film-layer during the deposition process, and may include one or more biodegradable polymers, such as, for example, polycarboxylic acid, polyanhydrides (e.g., maleic anhydride polymers), polyorthoesters, poly-amino acids, poly(carbonate), polyethylene oxide, poly(glutarunic acid), polyphosphazenes, polylactic acid, polyglycolic acid, poly(L-lactic acid), poly (D,L,-lactide), poly (lactide acid-co-glycolic acid), 50/50 (DL-lactide-co-glycolide), polydioxanone, polypropylene fumarate, polydepsipeptides, polycaprolactone, (D,L,-lactide-co-caprolactone), poly-caprolactone co-butlacrylate, polyhydroxybutyrate valerate, polycarbonates (e.g., tyrosine-derived polycarbonates and arylates), polyiminocarbonates, cyanoacrylate, calcium phosphates, poluglycosaminogycans, polysaccharides (e.g., hyaluronic acid, cellulose, and hydroxypropylmethyl cellulose), gelatin, starches, dextrans, alginates, proteins, polypeptides, surface erodible polymers (e.g., polyhydroxybutyrate, polycaorolactone, polyanhydrides (both crystalline and amorphous), maleic anhydride copolymers, and zinc-calcium phosphate), copolymers thereof, derivatives thereof, mixtures thereof, and the like.

In accordance with another aspect of the present invention, the device optionally may incorporate one or more therapeutic agents intended for local or systemic delivery. When a device is delivered into the body, the therapeutic agent may be at least temporarily stored in the device. In some variations, the therapeutic agent may diffuse out of the device. In other variations where the device is biodegradable, the therapeutic agent may be released from the device as the device biodegrades. The selection of therapeutic agent or agents, the timing of delivery, and the overall amount of therapeutic agent released from the device may be determined by the intended treatment plan, and a specific composition for the device may be chosen to achieve this release profile. In variations where the device includes one or more additional components (e.g., a plasticizer, a film-forming agent, etc.), any of the additional components may incorporate one or more therapeutic agents.

Examples of suitable therapeutic agents include, but are not limited to anti-inflammatory agents, anti-allergenic agents, anti-bacterial agents, anti-viral agents, anticholinergic agents, antihistamines, antithrombotic agents, anti-scarring agents, antiproliferative agents, antihypertensive agents, anti-restenosis agents, healing promoting agents, vitamins, biological molecules such as proteins, genes, growth factors, cells and DNA, combinations thereof, and the like.

Examples of suitable anti-allergenic agents that may be suitable for use with the described methods and devices include, but are not limited to, pemirolast potassium (ALAMAST®, Santen, Inc.) and any prodrugs, metabolites, analogs, homologues, congeners, derivatives, salts and combinations thereof. Examples of antiproliferative agents include, but are not limited to, actinomycin D, actinomycin IV, actinomycin 11, actinomycin Xl, actinomycin $C_1$, and dactinomycin (COSMEGEN®, Merck & Co., Inc.). Examples of healing promoting agents include, but are not limited to, sirolimus, everolimus, temsiolimus, and vitamin A.

Examples of antiproliferative agents that may be suitable for use with the described methods and devices include, but are not limited to, angiopeptin, angiotensin converting enzyme inhibitors such as captopril (CAPOTEN® and CAPOZIDE®, Bristol-Myers Squibb Co.), cilazapril or lisinopril (PRINIVIL® and PRINZIDE®, Merck & Co., Inc.); calcium channel blockers such as nifedipine; colchicines; fibroblast growth factor (FGF) antagonists, fish oil (omega 3-fatty acid); histamine antagonists; lovastatin (MEVACOR®, Merck & Co., Inc.); monoclonal antibodies including, but not limited to, antibodies specific for Platelet-Derived Growth Factor (PDGF) receptors; nitroprusside; phosphodiesterase inhibitors; prostaglandin inhibitors; suramin; serotonin blockers; steroids; thioprotease inhibitors; PDGF antagonists including, but not limited to, triazolopyrimidine; and nitric oxide, and any prodrugs, metabolites, analogs, homologues, congeners, derivatives, salts and combinations thereof.

Examples of anti-bacterial agents that may be suitable for use with the described methods and devices include, but are not limited to, aminoglycosides, amphenicols, ansamycins, β-lactams such as penicillins, lincosamides, macrolides, nitrofurans, quinolones, sulfonamides, sulfones, tetracyclines, vancomycin, and any derivatives or combinations thereof. Examples of penicillins that may be suitable for use with the described methods and devices include, but are not limited to, amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin G benzathine, penicillin G benzhydrylamine, penicillin G calcium, penicillin G hydrabamine, penicillin G potassium, penicillin G procaine, penicillin N, penicillin 0, penicillin V, penicillin V benzathine, penicillin V hydrabamine, penimepicycline, phenethicillin potassium, piperacillin, pivampicillin, propicillin, quinacillin, sulbenicillin, sultamicillin, talampicillin, temocillin, and ticarcillin.

Examples of anti-viral agents suitable for use with the described methods and devices include, but are not limited to, acyclovir, famciclovir, valacyclovir, edoxudine, ganciclovir, foscamet, cidovir (vistide), vitrasert, formivirsen, HPMPA (9-(3-hydroxy-2phosphonomethoxypropyl)adenine), PMEA (9-(2-phosphonomethoxyethyl)adenine), HPMPG (9(3-Hydroxy-2-(Phosphonomet--hoxy)propyl)guanine), PMEG (9-[2-(phosphonomethoxy)ethyl]guanine), HPMPC (1-(2-phosphonomethoxy-3-hydroxypropyl)cytosine), ribavirin, EICAR (5-ethynyl-1-beta-D-ribofuranosylimidazole-4-carboxamine), pyrazofurin (3-[beta-D-ribofuranosyl]-4-hydroxypyrazole-5-carboxamine), 3-Deazaguanine, GR92938X (1-beta-D-ribofuranosylpyrazole-3,4-dicarboxami--de), LY253963(1,3,4-thiadiazol-2-ylcyanamide), RD3-0028 (1,4-dihydro-2,3-Benzodithiin), CL387626 (4,4'-bis[4,6-d] [3-aminophenylN--,N-bis(2-carbamoylethyl)-sulfonilimino]-1,3,5-triazin-2-ylamino-biphenyl--2-,2'-disulfonic acid disodium salt), BABIM (Bis[5-Amidino-2-benzimidazoly-I]-methane), NIH351, and combinations thereof.

Anti-inflammatory agents may include steroidal and nonsteroidal anti-inflammatory agents. Examples of suitable steroidal anti-inflammatory agents include, but are not limited to, 21acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinonide acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, any of their derivatives, and combinations thereof.

Examples of suitable nonsteroidal anti-inflammatory agents include, but are not limited to, COX inhibitors. These COX inhibitors may include COX-1 or COX nonspecific inhibitors such as, for example, salicylic acid derivatives, aspirin, sodium salicylate, choline magnesium trisalicylate, salsalate, diflunisal, sulfasalazine and olsalazine; paraaminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone. The COX inhibitors may also include selective COX-2 inhibitors such as, for example, diaryl-substituted furanones such as rofecoxib; diaryl-substituted pyrazoles such as celecoxib; indole acetic acids such as etodolac and sulfonanilides such as nimesulide).

Examples of suitable biomolecules include, but are not limited to, peptides, polypeptides and proteins; oligonucleotides; nucleic acids such as double or single standard DNA (including naked and eDNA), RNA, antisense nucleic acids such as antisense DNA and RNA, small interfering RNA (siRNA), and ribozymes, genes, carbohydrates. Nucleic acids may be incorporated into one or more vectors (including viral vectors), plasmids, liposomes, or the like.

Examples of suitable proteins include, but are not limited to serca-2 protein, monocyte chemoattractant proteins ("MCP-1") and bone morphogenic proteins ("BMPs"), such as, for example. BMP-2 (OP-1), BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15. These BMPs may be provided as homodimers, heterodimers, or combinations thereof. In some variations, molecules capable of inducing an upstream or downstream effect of a BMP may be provided. This may include, for example, one or more "hedgehog" proteins, or the DNA encoding them. Examples of suitable genes include, but are not limited to survival genes that protect against cell death (e.g., anti-apoptotic Bcl-2 family factors and Akt kinase); SERCA 2 gene; and combinations thereof. In some variations, one or more therapeutic agents may comprise one or more angiogenic factors, such as acidic and basic fibroblast growth factors, vascular endothelial growth factor, epidermal growth factor, vascular endothelial growth factor, epidermal growth factor, transforming growth factor and, platelet-derived endothelial growth factor, platelet-derived growth factor, tumor necrosis factor, hepatocyte growth factor, and insulin like growth factor. In some variations, a therapeutic agent may comprise one or more cell cycle inhibitors (e.g., a cathepsin D (CD) inhibitor). Examples of suitable anti-restenosis agents include, but are not limited to, Rb, nFkB and E2F decoys, thymidine kinase ("TK"), combinations thereof, and the like.

Examples of suitable small molecules include, but are not limited to, hormones, nucleotides, amino acids, sugars, and lipids and compounds have a molecular weight of less than 100 kD. Examples of suitable cells include, but are not limited to, stem cells, progenitor cells, endothelial cells, adult cardiomyocytes, smooth muscle cells, side population (SP) cells, lineage negative (Lin-) cells (e.g., Lin-CD 34–, Lin-CD34+,Lin-cKit+, and the like), mesenchymal stem cells including mesenchymal stem cells with 5-aza, cord blood cells, cardiac or other tissue derived stem cells, whole bone marrow, bone marrow mononuclear cells, whole bone marrow, bone marrow mononuclear cells, endothelial progenitor cells, skeletal myoblasts or satellite cells, muscle derived cells, go cells, endothelial cells, adult cardiomyocytes, fibroblasts, smooth muscle cells, adult cardiac fibro blasts +5-aza, genetically modified cells, tissue engineered grafts, MyoD scar fibroblasts, pacing cells, embryonic stem cell clones, embryonic stem cells, fatal or neonatal cells, immunologically masked cells and teratoma derived cells. Cells may be of human origin (autologous or allogenic), of animal origin (xenogenic), or may be genetically engineered. Any of the foregoing drugs or biologically active molecules may be encapsulated, for example, in microparticles or liposomes, prior to incorporation within the device.

Other bioactive agents useful in the present invention include, but are not limited to, free radical scavengers; nitric oxide donors; rapamycin; methyl rapamycin; everolimus; tacrolimus; 40-O-(3-hydroxy)propyl-rapamycin;40-O-[2-(2-hydroxy)ethoxy]ethyl-rapamycin; tetrazole containing rapamycin analogs; estradiol; clobetasol; idoxifen; tazarotene; alpha-interferon; host cells including, but not limited to prokaryotes and eukaryotes such as, for example, epithelial cells and genetically engineered epithelial cells; patient's own platelet rich plasma, dexamethasone; and, any prodrugs, metabolites, analogs, homologues, congeners, derivatives, salts and combinations thereof.

EXAMPLE

Two compositions in accordance with the principles of the present invention were prepared using commercially available fibrinogen, thrombin, calcium chloride, PEG, a drug, and ethanol. As will be apparent from observing the table below, Compositions 1 and 2 are identical except the amount of ethanol is 2.5 ml in Composition 1 and 7.5 ml in Composition 2.

|  | Fibrinogen (mg) | Thrombin (U) | Calcium chloride (mg) | PEG (mg) | Drug content (mg) | Total ethanol content (ml) | Ambient humidity (%) |
| --- | --- | --- | --- | --- | --- | --- | --- |
| Composition 1 | 78 | 60 | 13.2 | 30 | 2 | 2.5 | 68 |
| Composition 2 | 78 | 60 | 13.2 | 30 | 2 | 7.5 | 68 |

Compositions 1 and 2 were separately poured in a plastic mold having a surface area of 10 cm². Composition 1 was dried using a vacuum to substantially eliminate the 2.5 ml of ethanol to form Film-Layer 1. Composition 2 was dried in the same drying conditions as Composition 1 to substantially eliminate the 7.5 ml of ethanol to form Film-Layer 2.

Figure 10:
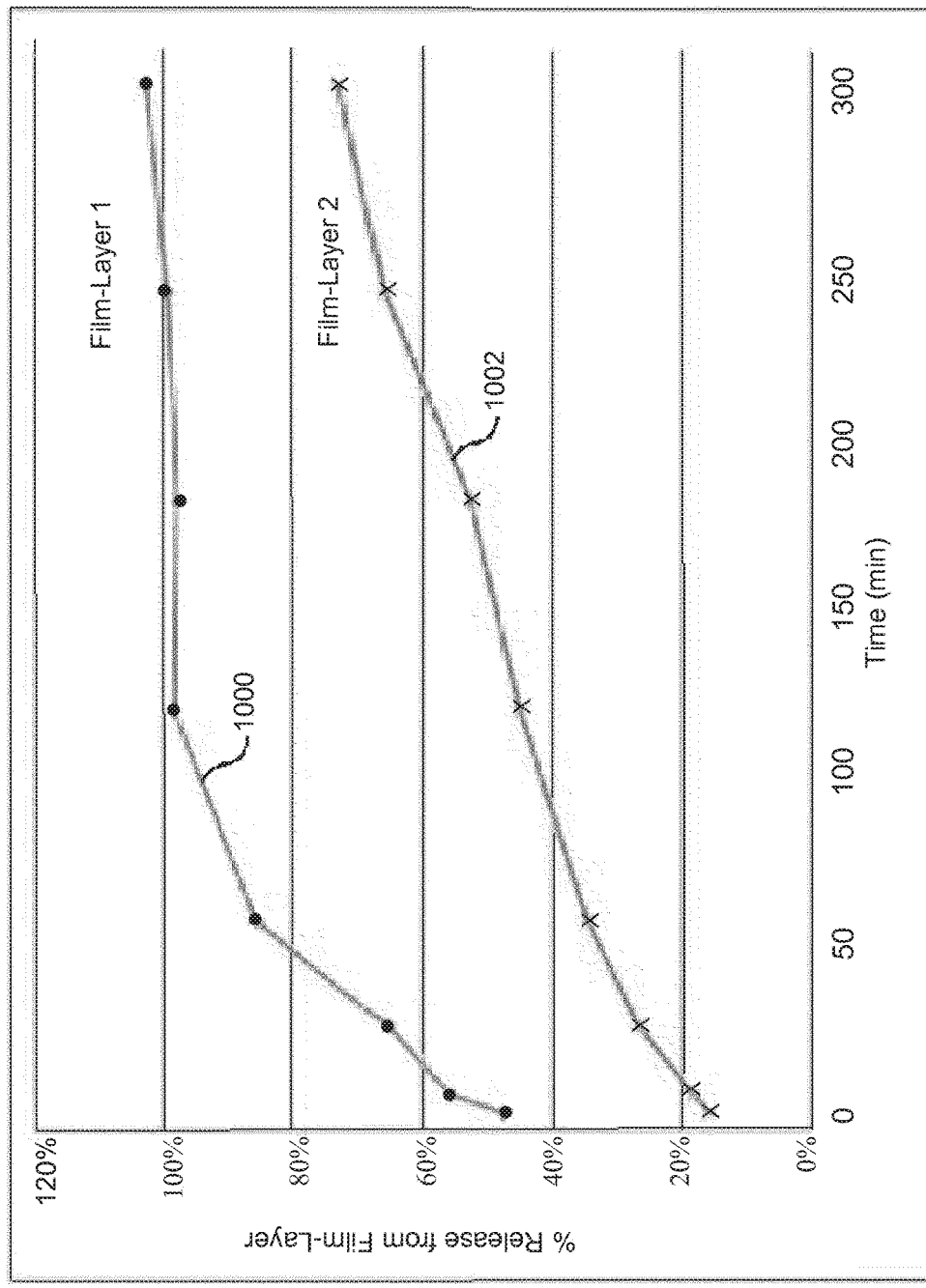
FIG. 10 is a graph showing the percentage of drug release from exemplary film-layers as a function of time.

The drug release times from Film-Layer 1 and Film-Layer 2 were analyzed in a buffered saline using a reference front high performance liquid chromatography ("RF-HPLC") system. FIG. 10 is a graph showing the percentage of drug release from a film-layer over time in minutes. Release time 1000 depicts the percentage of drug release from Film-Layer 1 over time and release time 1002 depicts the percentage of drug release from Film-Layer 2 over time. As will be apparent from observing FIG. 10, Film-Layer 2 (initially formed with higher ethanol content) has a significantly slower drug release profile than Film-Layer 1.

Figure 11:
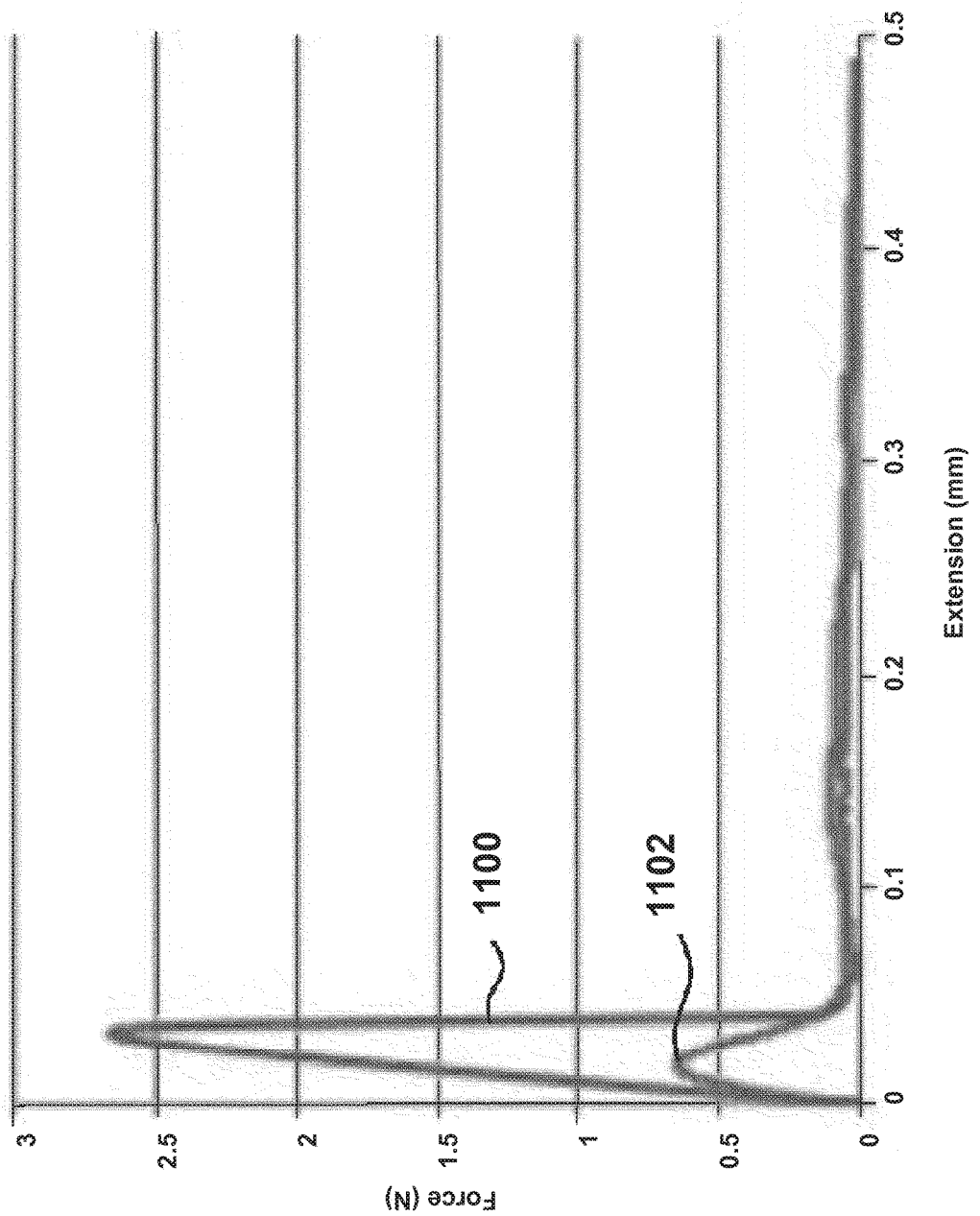
FIG. 11 is a graph showing the force by extension of exemplary film-layers for analyzing adhesive properties.

The adhesive properties of 450 mm² samples of Film-Layer 1 and Film-Layer 2 when applied to collagen films were analyzed using an Instron machine. FIG. 11 is a graph showing the force in Newtons by extension in millimeters of Film-Layer 1 and Film-Layer 2. Adhesive line 1100 depicts the force required to extend Film-Layer 1 a distance and adhesive line 1102 depicts the force required to extend Film-Layer 2 a distance. As will be apparent from FIG. 11, Film-Layer 1 (initially formed with lower ethanol content) has higher adhesive properties than Film-Layer 2.

Surprisingly, although Film-Layer 1 and Film-Layer 2 have significantly different mechanical characteristics, as demonstrated in FIGS. 10 and 11, the specimens of each of Film-Layer 1 and Film-Layer 2 appear substantially identical when viewed using an optical microscope.

While various illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. A method for applying a device in a sinus of a patient, the method comprising:
advancing the device comprising a first film-layer and a second film-layer to the sinus, the first film-layer comprising fibrinogen and a first therapeutic agent, the second film-layer comprising fibrinogen and a second therapeutic agent;
applying the device on sinus tissue in the sinus;
releasing the first therapeutic agent into the sinus tissue from the first film-layer at a first release profile; and
releasing the second therapeutic agent into the sinus tissue from the second film-layer at a second release profile different from the first release profile; and
wherein the first film-layer is formed by processing a first composition comprising the fibrinogen, the first therapeutic agent, and a first amount of non-aqueous solvent and the second film-layer is formed by processing a second composition comprising the fibrinogen, the second therapeutic agent, and a second amount of non-aqueous solvent different from the first amount of non-aqueous solvent.

2. The method of claim 1, wherein applying the device to the sinus tissue comprises applying the device to the sinus tissue after sinus surgery.

3. The method of claim 1, wherein applying the device to the sinus tissue comprises applying the device to the sinus tissue of the patient suffering from sinusitis.

4. The method of claim 1, wherein the first and second film-layers further comprise calcium salt.

5. The method of claim 4, wherein the calcium salt comprises calcium chloride.

6. The method of claim 1, wherein the first and second film-layers further comprise polyethylene glycol.

7. The method of claim 1, wherein the first film-layer has a first amount of therapeutic agent and the second film-layer has a second amount of the second therapeutic agent different from the first amount.

8. The method of claim 1, wherein the first film-layer and the second film-layer are bonded using an intermediate layer disposed between the first film-layer and the second film-layer.

9. The method of claim 8, wherein the intermediate layer is configured to dissolve to create a reservoir, pores, void, or channel between the first film-layer and the second film-layer.

10. The method of claim 1, wherein the first therapeutic agent or the second therapeutic agent or both comprise one or more anti-inflammatory agents, anti-allergenic agents, anti-bacterial agents, anti-viral agents, anticholinergic agents, antihistamines, antithrombotic agents, anti-scarring agents, antiproliferative agents, antihypertensive agents, anti-restenosis agents, healing promoting agents, vitamins, proteins, genes, growth factors, cells, RNA, or DNA.

11. The method of claim 1, wherein the first therapeutic agent or the second therapeutic agent or both comprise a steroidal anti-inflammatory agent.

12. The method of claim 1, wherein the first therapeutic agent or the second therapeutic agent or both are fluticasone propionate.

13. The method of claim 1, wherein the first therapeutic agent and the second therapeutic agent are the same type of therapeutic agent.

14. The method of claim 1, wherein the device is configured to form a fibrin patch upon exposure to moisture in the sinus.

15. The method of claim 1, wherein the first film-layer or the second film-layer or both further comprise thrombin mixed with the fibrinogen.

16. The method of claim 1, wherein the first film-layer or the second film-layer or both are coated with a protective layer.

17. The method of claim 1, wherein the first film-layer and the second film-layer are configured to biodegrade within the sinus.

18. The method of claim 1, wherein advancing the device comprises advancing the device using a delivery device, and wherein applying the device to the sinus tissue comprises deploying the device from the delivery device.

19. The method of claim 1, wherein applying the device to the sinus tissue comprises applying the device to the sinus tissue to promote healing of iatrogenic wounds and reduce formation of post-operative lesions.

* * * * *